US008777890B2

(12) United States Patent
Brandeis

(10) Patent No.: US 8,777,890 B2
(45) Date of Patent: *Jul. 15, 2014

(54) DEVICE FOR LIQUID MEDICAL SUBSTANCE VENOUS ADMINISTRATION

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,182

(22) Filed: Jan. 28, 2013

(65) Prior Publication Data

US 2013/0144205 A1 Jun. 6, 2013

Related U.S. Application Data

(63) Continuation of application No. 12/918,331, filed as application No. PCT/IL2009/000197 on Feb. 19, 2009, now Pat. No. 8,361,008.

(60) Provisional application No. 61/029,930, filed on Feb. 20, 2008, provisional application No. 61/050,644, filed on May 6, 2008.

(51) Int. Cl.
*A61M 1/00* (2006.01)

(52) U.S. Cl.
USPC ............... 604/27; 604/28; 604/35; 604/38

(58) Field of Classification Search
USPC ............... 604/27, 30, 35, 101.03–101.05, 604/102.01–102.03, 500, 506–508, 523, 28, 604/38
See application file for complete search history.

(56) References Cited

U.S. PATENT DOCUMENTS

| 6,022,336 A | 2/2000 | Zadno-Azizi et al. |
| 6,461,327 B1 * | 10/2002 | Addis et al. ............... 604/101.04 |
| 6,635,027 B1 | 10/2003 | Cragg et al. |
| 8,361,008 B2 * | 1/2013 | Brandeis ..................... 604/27 |
| 2005/0245896 A1 | 11/2005 | Kucharczyk et al. |
| 2006/0129091 A1 | 6/2006 | Bonnette et al. |

FOREIGN PATENT DOCUMENTS

| JP | 2006-511256 | 4/2006 |
| WO | WO 2004/037178 | 5/2004 |
| WO | WO 2006/017470 | 2/2006 |
| WO | WO 2006/063180 | 6/2006 |
| WO | WO 2009/104189 | 8/2009 |

OTHER PUBLICATIONS

Translation of Notice of Reason for Rejection Dated Apr. 9, 2013 From the Japanese Patent Office Re. Application No. 2010-547301.

(Continued)

*Primary Examiner* — Theodore Stigell

(57) ABSTRACT

A method for administering a liquid medical substance in a vein. The method comprises inserting a plurality of tubular ducts into a target venous lumen, conducting a liquid medical substance via at least one of the plurality of tubular ducts (106, 215, 419, 602) for the administering thereof toward a venous wall (110, 410) at the target venous lumen in an ejection pressure, quantity and direction, and withdrawing a residue of the liquid medical substance from the target venous lumen, in a suction pressure, quantity and direction, for the conducting thereof via at least one different of the plurality of tubular ducts (130, 240, 400). A relation between the ejection pressure, quantity and direction and the suction pressure, quantity and direction limits the extent of the administering within the venous lumen to a predefined space.

27 Claims, 6 Drawing Sheets

(56) References Cited

OTHER PUBLICATIONS

Communication Relating to the Results of the Partial International Search Dated Jun. 26, 2009 From the International Searching Authority Re.: Application No. PCT/IL2009/000197.

International Preliminary Report on Patentability Dated Sep. 2, 2010 From the International Bureau of WIPO Re. Application No. PCT/IL2009/000197.

International Search Report and the Written Opinion Dated Nov. 10, 2009 From the International Searching Authority Re.: Application No. PCT/IL2009/000197.

Notice of Allowance Dated Sep. 28, 2012 From the US Patent and Trademark Office Re. U.S. Appl. No. 12/918,331.

Official Action Dated Jun. 20, 2012 From the US Patent and Trademark Office Re. U.S. Appl. No. 12/918,331.

Official Decision of Rejection Dated Jan. 17, 2014 From the Japanese Patent Office Re. Application No. 2010-547301 and Its Translation Into English.

* cited by examiner

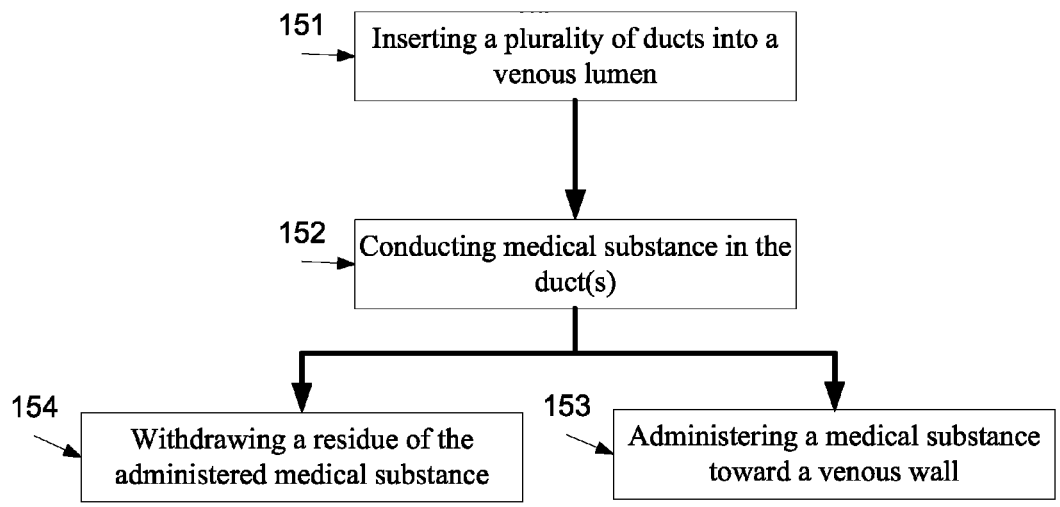
FIG. 2
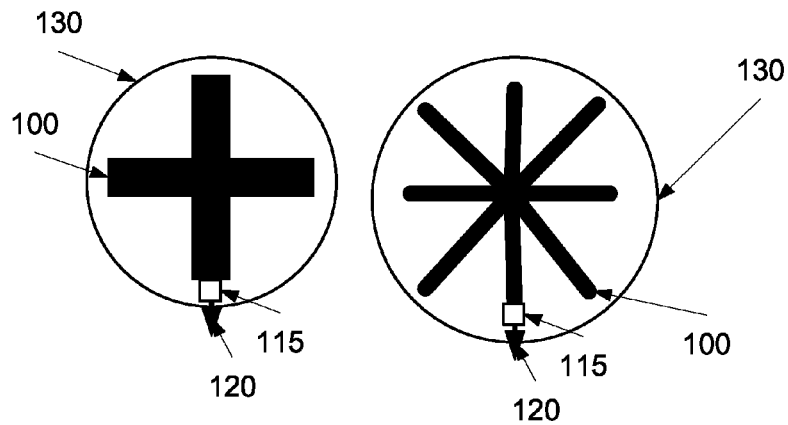
FIG. 3A  FIG. 3B
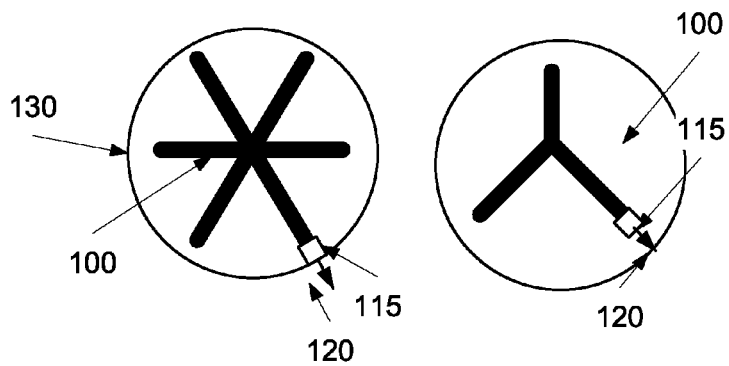
FIG. 3C  FIG. 3D

DEVICE FOR LIQUID MEDICAL SUBSTANCE VENOUS ADMINISTRATION

RELATED APPLICATIONS

This application is a continuation of U.S. patent application Ser. No. 12/918,331 filed on Aug. 19, 2010, now U.S. Pat. No. 8,361,008, which is a National Phase of PCT Patent Application No. PCT/IL2009/000197 having International filing date of Feb. 19, 2009, which claims the benefit of priority of U.S. Provisional Patent Application Nos. 61/050,644 filed on May 6, 2008, and 61/029,930 filed on Feb. 20, 2008. The contents of the above applications are all incorporated herein by reference.

FIELD AND BACKGROUND OF THE INVENTION

The present invention, in some embodiments thereof, relates to method and device of administering liquid medical substances and, more particularly, but not exclusively, to method and device of administering liquid medical substances in blood vessel.

Administration of liquid medical substances directly into venous lumen for treating blood vessels, for example for sclerotherapy, has been practiced for a number of years.

For example, sclerotherapy is used for eliminating large spider veins (telangiectasiae) and smaller varicose leg veins. The sclerosing solution closes the "feeder veins" under the skin that are causing the spider veins to form, thereby making a recurrence of the spider veins in the treated area less likely. Sclerotherapy can also be performed using sclerosants, such as microfoam sclerosants, under ultrasound guidance to treat larger varicose veins, including the great and small saphenous veins, see Paul Thibault, Sclerotherapy and Ultrasound-Guided Sclerotherapy, The Vein Book/editor, John J. Bergan, 2007, which is incorporated herein by reference. After a map of the patient's varicose veins is created using ultrasound, these veins are injected whilst real-time monitoring of the injections is undertaken, also using ultrasound. The sclerosant can be observed entering the vein, and further injections performed so that all the abnormal veins are treated. Follow-up ultrasound scans are used to confirm closure of the treated veins, and any residual varicose veins can be identified and treated.

One of the limitations sclerosing treatments for veins the concentration of the used sclerosing agents in certain target blood vessels. For example, some regulatory limitations restrict the concentration of sclerosing agents to less than 3% concentration if the target vein is less than 4 mm in diameter. In such concentrations, the sclerosing agent is rapidly diluted and therefore not sufficiently effective for treating the surrounding veins. Increasing the quantity and/or the concentration of the injected sclerosing agent to offset the dilution may introduce harmful quantities into the body.

It should be noted that foaming techniques have also been tried to treat veins using sclerosing agents. The delivering of sclerosing agents in a foam form at least partially offsets the effect of the sclerosant dilution. However, significant harmful effects resulting from the foamed sclerosants have been evidenced, in particular blood clotting throughout the vascular system, wherever the foamed sclerosant has reached.

Few devices and method have been developed for improving the administration of liquid medical substances, such as sclerosing agents, into the veins. For example, International Patent Application No. WO 2006/017470A2, published on 16 Feb. 2006, which is incorporated herein by reference describes a device and method for treating bodily diseases and/or conditions, for example, varicose veins, tumors and aneurisms including for example insertion of a blocking device toward a target destination using an intrabody device, such as a catheter, and delivery of sclerosing or other agents to the vessel while maintaining minimal, for example zero pressure in the treatment area. The blocking device may prevent treatment materials, embolisms, debris and the like from entering the upstream section of vessel. The blocking device may include, for example, a cap or other concave shape and may be expandable or extendible towards the vessel walls.

SUMMARY OF THE INVENTION

According to some embodiments of the present invention there is provided a method for administering a liquid medical substance in a vein. The method comprises inserting a plurality of tubular ducts into a target venous lumen, conducting a liquid medical substance via at least one of the plurality of tubular ducts for the administering thereof toward a venous wall at the target venous lumen in an ejection pressure, quantity and direction, and withdrawing a residue of the liquid medical substance from the target venous lumen, in a suction pressure, quantity and direction, for the conducting thereof via at least one different of the plurality of tubular ducts. A relation between the ejection pressure, quantity and direction and the suction pressure, quantity and direction limits the extent of the administering within the venous lumen to a predefined space.

Optionally, the liquid medical substance comprises a sclerosing agent.

More optionally, the sclerosing agent concentration is lower than 5 percent.

Optionally, the withdrawing and the administering are performed simultaneously.

Optionally, the withdrawing is performed a predefined period after the administering being completed.

Optionally, at least one of the ejection pressure, quantity and direction and the suction pressure, quantity and direction is performed according to a characteristic of the target venous lumen.

Optionally, the ejection direction is substantially perpendicular to movement axis of the venous wall.

Optionally, the administering is performed in a plurality of ejection directions.

Optionally, the plurality of tubular ducts are connected to an intrabody device tip at least one of the administering and withdrawing is performed via the intrabody device tip while the intrabody device tip being in motion.

Optionally, at least one of the administering and withdrawing is performed in a helical pattern having a central axis substantially parallel to the venous wall.

Optionally, the administering comprises substantially blocking a blood flow in the target venous lumen.

Optionally, the withdrawing is applied from a plurality of suction directions.

More optionally, wherein a first of the plurality of suction directions is directed toward a first edge of the venous lumen and a second of the plurality of suction directions is directed toward a second edge of the venous lumen.

According to some embodiments of the present invention there is provided an intrabody device for administering a liquid medical substance in a vein. The intrabody device comprises at least one outlet and at least one inlet, an ejection force source connected to at least one tubular duct and configured for applying an ejection force for conducing therethrough a liquid medical substance to the at least one outlet for administering the liquid medical substance at an ejection pressure, quantity and direction, and a suction force source connected to at least one tubular duct and configured for applying a suction force for withdrawing therethrough a residue of the liquid medical substance from the at least one inlet in a suction pressure, quantity and direction. When the at least one inlet and outlet are in a venous lumen and a relation between the ejection and suction pressure, quantity and direction limits the extent of the liquid medical substance within the venous lumen to a predefined space.

Optionally, the intrabody device further comprises an ejection channel with the at least one outlet and a withdrawal channel with the at least one inlet at the tip of the intrabody device, the withdrawal channel is partly encircled by the ejection channel.

Optionally, the at least one inlet comprising a plurality of inlets, the at least one outlet is positioned between at least two of the plurality of inlets.

Optionally, the intrabody device further comprises a helical ejection channel having the at least one outlet positioned therealong.

Optionally, the intrabody device further comprises a helical withdrawal channel having the at least one inlet positioned therealong.

Optionally, the intrabody device further comprises a filtering element positioned in front of the at least one inlet and configured for preventing from at least one component having a diameter above a certain threshold from penetrating the at least one inlet.

Optionally, the intrabody device further comprises a filtering element positioned in front of the at least one inlet and configured for determining at least one of the suction pressure, quantity and direction.

Optionally, the filtering having a cavity for collecting the at least one component.

Optionally, the intrabody device further comprises a filtering element positioned in front of the at least one outlet and configured for determining at least one of the ejection pressure, quantity and direction.

Optionally, the intrabody device further comprises an intrabody device tip having a portion having the at least one outlet and an expended and unexpended configurations, wherein a distance between the at least one outlet and a venous wall in the venous lumen is reduced when the portion being in the expended configuration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a flowchart of a method for administering a liquid medical substance, such as a sclerosing agent, in a limited space in a venous lumen, according to some embodiments of the present invention;

FIGS. 3A-3D are axial sectional views of exemplary intrabody device tips, according to some embodiments of the present invention;

DESCRIPTION OF EMBODIMENTS OF THE INVENTION

Figure 1:
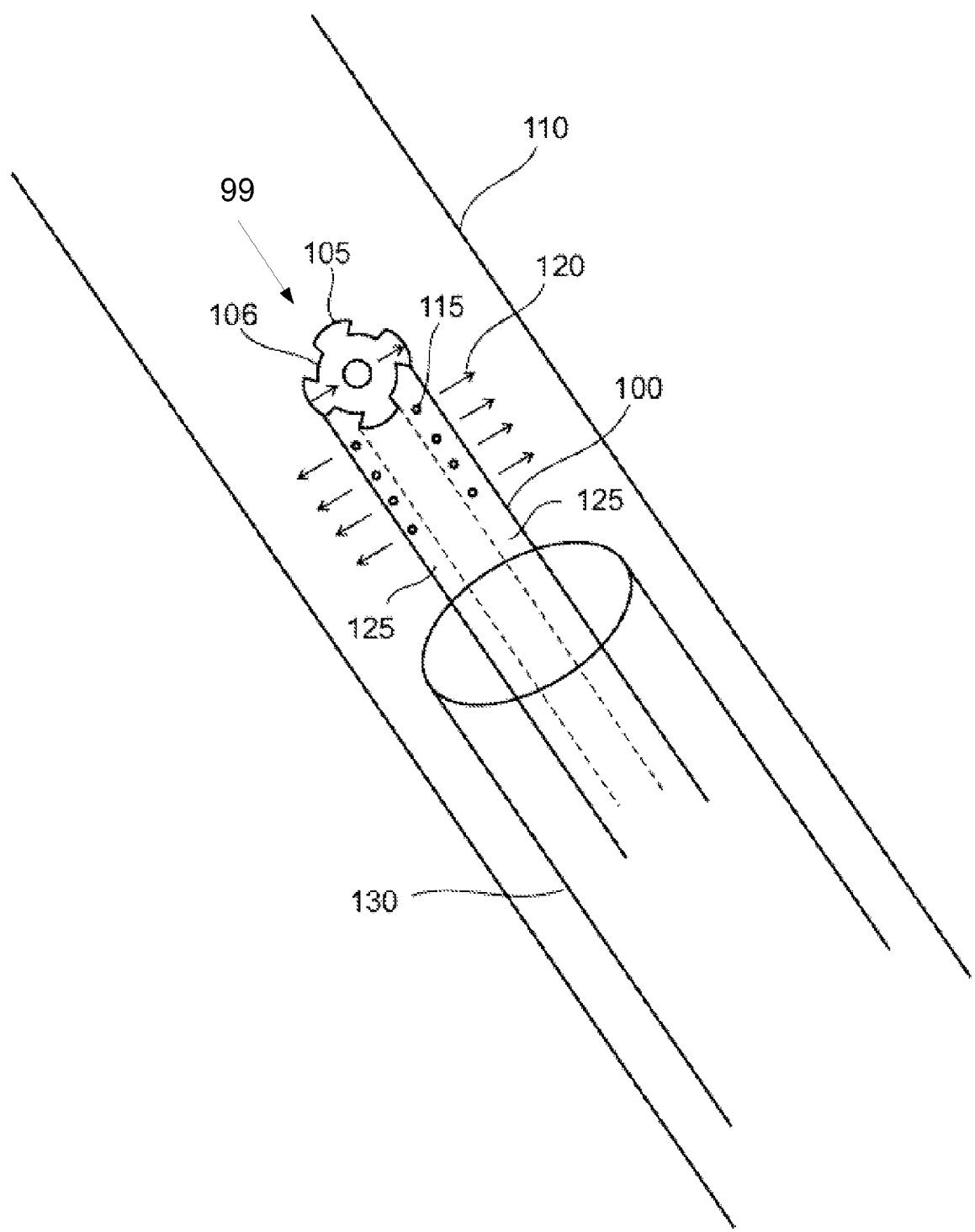
FIG. 1 is a schematic illustration of an exemplary intrabody device tip for administering and extracting a liquid medical substance, such as a sclerosing agent, according to some embodiments of the present invention.

The present invention, in some embodiments thereof, relates to method and device of administering liquid medical substances and, more particularly, but not exclusively, to method and device of administering liquid medical substances in blood vessel.

According to some embodiment of the present invention there is provided a method for administering a liquid medical substance, such as a sclerosing agent, in a vein. The method may be implemented using an intrabody device, such as a catheter, having an insertion tube with a plurality of tubular ducts which is inserted into a target venous lumen. Such a positioning allows administering a liquid medical substance towards a venous wall at the target venous lumen in an ejection pressure, quantity and direction which optionally predefined. In addition, optionally simultaneously, alternatively, and/or sequentially a residue of the liquid medical substance is drawn from the target venous lumen, for example together with blood and debris. The withdrawing is performed via one or more of the inserted plurality of tubular ducts in a suction pressure, quantity and direction, which is optionally predefined. The relation between the ejection pressure, quantity and direction and the suction pressure, quantity and direction limits the extent of the administering of the liquid medical substance within the venous lumen to a predefined space.

According to some embodiment of the present invention there is provided an intrabody device, such as a catheter, for administering a liquid medical substance in a vein. The intrabody device comprises one or more outlets and inlets, for example situated in a distal end of the catheter. The intrabody device comprises an ejection force source, such as a piston, which is connected to one or more tubular ducts and configured for applying an ejection force for conducing a liquid medical substance through the tubular ducts to one or more of the outlets. In such a manner, the administering of the liquid medical substance at an ejection pressure, quantity and direction is allowed. The intrabody device further comprises a suction force source, such as a piston, which is connected to one or more tubular ducts and configured for applying a suction force for withdrawing through the one or more tubular ducts a residue of the liquid medical substance via the one or more inlets in a suction pressure, quantity and direction. When the inlets and outlets are in a venous lumen a relation between the pressure, quantity and direction of the ejection and the pressure, quantity and direction of the suction limits the extent of the liquid medical substance within the venous lumen to a predefined space.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1 which is a schematic illustration of an exemplary intrabody device tip 99 of an intrabody device, such as a catheter, (not shown) for administering and extracting a liquid medical substance, such as a sclerosing agent, according to some embodiments of the present invention. The intrabody device tip 99 is attached at a distal end of the intrabody device, such as a catheter. For clarity, a liquid medical substance means a liquid comprising one or more of the following a sclerosing agent, such as sodium tetradecyl sulfate (STS), polydocanol, and bleomycin, a drug, a medical component, a filling, such as hyaluronic acid (HA) secretion and collagen, a medical agent and/or any combination thereof. For example, a liquid medical substance may be a medicament for repairing, re-shaping, restructuring, curing, disinfecting, occluding and ablating a target vein, a venous wall 110 of a vein and/or an organ in a proximity to a target vein. Similar treatments may be performed for vessels, lumen or anatomical areas adjacent to veins. In some embodiments treatments may be implemented in target vein, for example, perforator vein, varicose vein, spider vein, saphenous vein, varicose-selle vein, a hemorrhoid, and/or a vein ablation.

Optionally, the intrabody device tip 99 is connected to an insertion tube having a plurality of tubular ducts which are aligned therealong. One or more of the tubular ducts are tubular administration ducts which are adapted for conducting fluid, such as a liquid medical substance, to the intrabody device tip 99. One or more of the tubular ducts are tubular extraction ducts for withdrawing fluid, such as a residue of the conducted liquid medical substance, from the intrabody device tip 99. As used herein, a residue of the liquid medical substance means a liquid medical substance which has been administered via the intrabody device tip 99 and is present in the venous lumen in proximity to the intrabody device tip 99, for example the blood which is blended, mixed, and/or diluted with the administered liquid medical substance, the liquid medical substance which have been released from the venous walls 110 after a reaction therewith, the liquid medical substance which have not been in contact with the venous walls 110 and/or any solution that includes a residue of the liquid medical substance.

Optionally, the intrabody device tip 99 comprises an administration channel 100, such as a needle, for introducing the liquid medical substance in a venous space. The administration channel 100 forms a tubular administration duct 106 which is connected to conducting ducts of the insertion tube of the intrabody device, such as a catheter. Optionally, the tubular administration duct 106 comprises a plurality of outlets 115, such as apertures or nozzles, for example 0.4-1.2 mm diameter holes, for administering the liquid medical substance in proximity to the venous walls. For example, the plurality of outlets 115 may be substantially perpendicular to the main axis of the administration channel 100, which is directed toward the venous walls.

In such a manner, liquid medical substances, such as sclerosing agents, are released toward the venous walls 120, in proximity to a target venous wall, and do not get away to other organs, tissues and/or blood vessels. In addition, by using a plurality of outlets 115 which are directed toward a venous wall, the released liquid medical substance may be in relatively low concentration and still affect the venous walls as the blood in the venous lumen does not substantially dilute released liquid medical substance before it contacts the venous walls.

The intrabody device tip 99 comprises an extraction channel 130 configured for withdrawing the released liquid medical substance, for example with blood and/or debris, from the proximity of the venous walls. Optionally, the administration channel 100 is encircled by the extraction channel 130. Optionally, the axial shape of the administration channel 100 is a cross or a star with a plurality of projections, for example as shown at 105. In such a manner, one or more lumens between the inner walls of the extraction channel 130 and the outer walls 125 of the administration channel 100 are maintained.

In some embodiments of the present invention, the administration channel 100 administers the medical substance is a selected ejection pressure, quantity and direction and the extraction channel 130 draws the residue of the medical substance is a selected suction pressure, quantity and direction. In such a manner, the released liquid medical substance does not get away from a limited space at the venous lumen, around the intrabody device tip 99, for example a limited space of 1 cubic centimeter, 2 cubic centimeter, 3 cubic centimeter, 4 cubic centimeter and/or any intermediate or smaller space which is centered around any of the outlets.

Optionally, the ejection pressure, quantity and/or direction and the suction pressure, quantity and/or direction may be determined according to clinical experiments and/or a numerical simulation of the medical substance in various venous lumens. Optionally, the ejection pressure, quantity and/or direction and/or the suction pressure, quantity and/or direction are determined according to the target vein in which the administration is performed. As different veins have different characteristics, such as width and/or an estimated blood flow, the pressure, quantity and/or direction of the suction and/or ejection may be changed. For example, the ejection pressure, quantity and/or direction and/or the suction pressure, quantity and/or direction may be set differently at the great saphenous vein or at the small saphenous vein.

Reference is now made to FIG. 2, which is a flowchart of a method for administering a liquid medical substance, such as a sclerosing agent, in a limited space in a venous lumen, according to some embodiments of the present invention.

First, as shown at 151, one or more tubular administration ducts and tubular extraction ducts are inserted into a target vein. For example, the tubular ducts may be channels of an intrabody device, such as a catheter. Optionally, a tubular administration duct is a channel having a first diameter and positioned in a tubular withdrawing duct, such as channel having a second diameter, which is larger than the first average diameter or vice versa.

As shown at 152, one or more tubular administration ducts allows the conducting of a liquid medical substance for the administration thereof into a target venous lumen in the target vein, for example via the administration channel 100, as shown at 153. The tubular administration duct is connected to the aforementioned administration channel 100 and allows the administering of the liquid medical substance in a limited space, for example as described above.

It should be noted that an estimated response of the target vein to the presence of the intrabody device, such as a catheter, in the vein is a collapse of the venous walls 110 toward the intrabody device tip 99 and the intrabody device, such as a catheter's insertion tube. Such a collapse brings the venous walls towards the outlets 115 of the administration channel 100 and allows releasing the liquid medical substance, which are optionally a sclerosing agent, substantially in proximity to the venous walls. For example, a vein treatment procedure may include maneuvering and/or positioning the intrabody device, such as a catheter, such that the vein may be responsively collapsed, thereby causing direct contact between the intrabody device tip 99 and the venous walls. In such an embodiment, application or administration of the sclerosing agent substantially adjacently to the venous walls 140 may rapidly and/or more effectively trigger irritation, inflammation, and/or destruction thereof. In addition, the short distance between the outlets venous walls 140, which is optionally less than 2 millimeter or 1 millimeter during the administration, may allow using a relatively small quantity and/or low concentration of the released sclerosing agent.

As shown at 154, simultaneously and/or sequentially the tubular extraction ducts are used for withdrawing, via the extraction channel 130 at the tip of the intrabody device 99, such as a catheter, a residue of the liquid medical substance from the limited space that confines the target venous. Optionally, the withdrawing is performed by applying a suction force into the target vein in proximity to the limited space. In such a manner, the withdrawing limits the administering to the limited space. The suction force may be applied by a piston and/or any other respective mechanism. The direction of the suction force is optionally defined by the inlets of the extraction channel 130. The pressure of the suction force and/or the quantity of the drawn residue are optionally defined by the diameter of the extraction channel 130, the diameter of the one or more ducts which are connected to the extraction channel 130 and/or the diameter of the inlets.

Optionally, the withdrawing 154 and the administering 153 are controlled by an intrabody device, such as a catheter, controller mechanism, such as a dual syringe. For example, the intrabody device, such as a catheter, controller mechanism may initiate a release procedure in which a liquid medical substance is pushed via the administration channel 100 and the residue of the liquid medical substance is drawn via an extraction channel 130 simultaneously, sequentially, alternatively, and/or according to a predefined releasing and/or withdrawing pattern.

As depicted in FIG. 1, the extraction channel 130 may surround the administration channel 100. In such an embodiment, the lumen between the extraction channel 130 and the administration channel 100 is used for withdrawing the residue of the liquid medical substance from the limited space that confines the target venous.

Reference is now also made to FIGS. 3A-3D; each is an axial sectional view of an exemplary intrabody device tip, according to some embodiments of the present invention. As depicted in FIGS. 3A-3D and in FIG. 1, the extraction channel 130, which is positioned in the extraction channel 130, has an axial sectional profile of a cross or a star, such as a 3 projections star, a 4 projections star, a 6 projections star, and an 8 projections star. The outlets the extraction channel 130 are optionally positioned on the tip of each one of the respective projections of the axial sectional profile, for example as shown at 115. In such a manner, the liquid medical substance is released toward the inner venous walls, for example as indicated by arrows 120.

The axial shape of the administration channel 100 may prevent kinks or twists of the extraction channel 130 as the projections of the administration channel 100 supports the positioning of the walls of the extraction channel 130 during the introduction of the intrabody device tip into the target vein.

It should be noted that the axial sectional profile of the administration channel 100 and/or the extraction channel 130 may be different, creating various ducts for extracting the residue of the liquid medical substance, optionally with surrounding blood and/or debris.

Optionally, the administration is performed after blocking one or more sides of the target vein, for example using a blocking device such as described in International Patent Application No. WO 2006/017470A2, published on 16 Feb. 2006, which is incorporated herein by reference.

Optionally, the administering 152 and/or the withdrawing 153 are performed while moving the intrabody device tip along the target vein. For example, the administering 152 and/or the withdrawing 153 are performed during the extraction and/or the insertion of the intrabody device tip 99. In such a manner, the area of the treated venous wall is increased and the residue of liquid medical substance may be removed more efficiently.

As the withdrawing operation 153 allows removing the residue of the administered liquid medical substance after the interaction thereof with the inner venous walls, agents, such as sclerosing agents, may be used in higher concentrations and/or activity level. The withdrawing operation 153 is performed before the of the administered liquid medical substance is spread, allowing the removal thereof from the blood circulation before a substantial clotting occurs and/or any other damage is caused to the body of a respective patient. For example, non-diluted or minimally diluted sclerosing agents may be used for sclerotherapy in veins having a diameter of more than 4, 5, and 6 millimeters, such as the great saphenous vein.

Figures 4A, 4B:
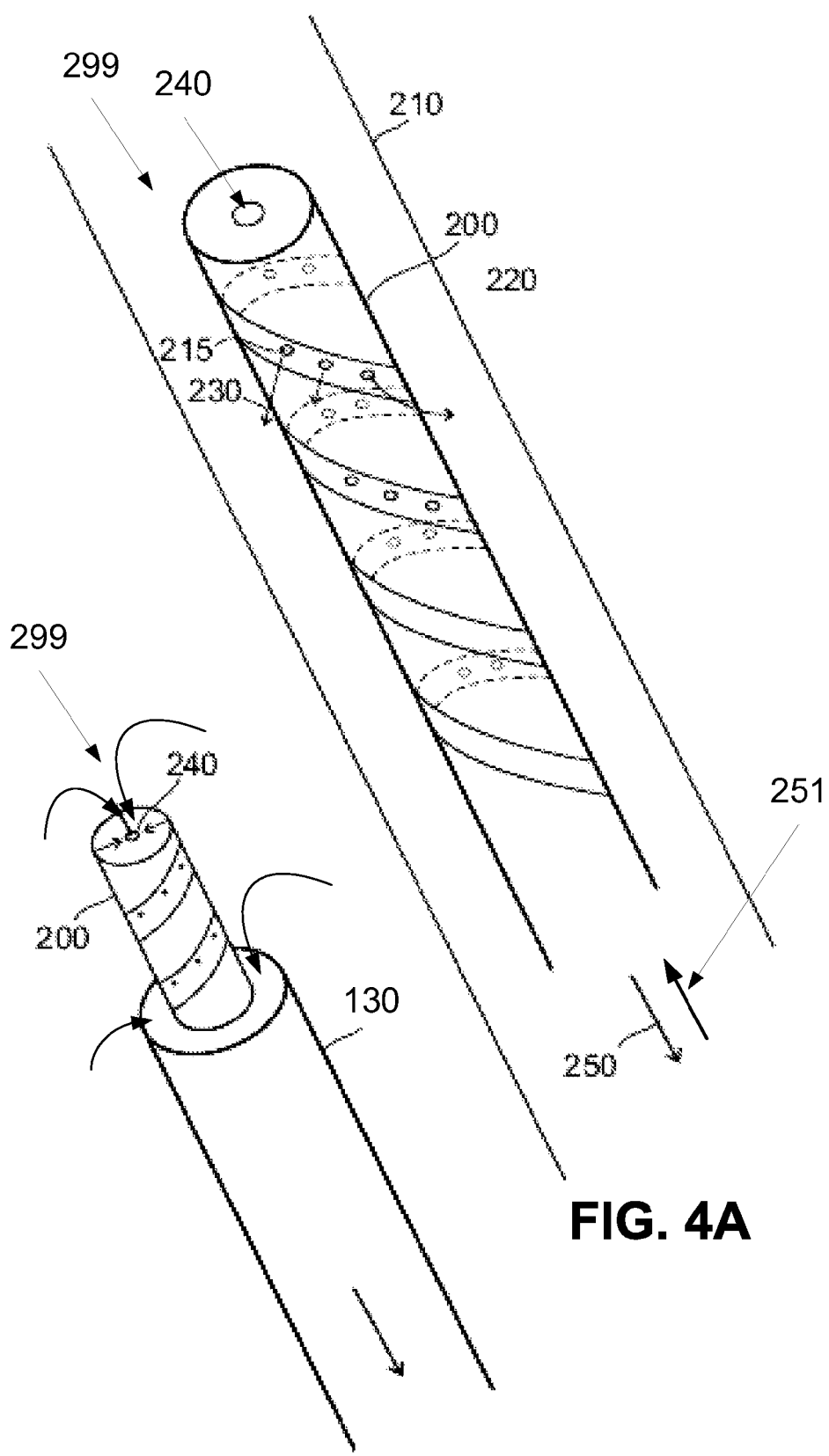
FIGS. 4A and 4B are schematic illustrations of an intrabody device tip having a helical arrangement of a plurality of outlets and/or inlets, according to some embodiments of the present invention.

Reference is now made to FIGS. 4A and 4B, which are schematic illustrations of an intrabody device tip 299 having a helical arrangement of a plurality of outlets 215 on a helical channel 200 for administering a liquid medical substance 230, such as a sclerosing agent and/or a plurality of inlets (not shown) for withdrawing the residue of the administered liquid medical substance, according to some embodiments of the present invention. Optionally, the arrangement comprises a plurality of outlets 215 which are formed on a helical channel 200 that is configured for conducting the liquid medical substance, similarly to the above mentioned administration channel 100. Optionally, the arrangement comprises a plurality of inlets, such as holes or nozzles, for example 0.4-1.2 mm diameter holes, which are formed on a helical channel 200 that is configured for withdrawing the residue of the administered liquid medical substance, similarly to the above mentioned extraction channel 130. It should be noted that if the arrangement comprises a plurality of outlets 215, the withdrawing may be performed via an extraction channel 130, such as the aforementioned extraction channel 130. Optionally, an additional withdrawing duct 240 is positioned in parallel to the central axis of the helical channel 200. Such an additional withdrawing duct 240 allows withdrawing the residue of the medical substance from the distal end of the intrabody device tip 299. In such a manner, the withdrawing limits the administered space to the venous lumen which is in front of the helical channel 200, which is optionally a needle shaped conductor with outlets which arranged in a helical pattern.

If the arrangement comprises a plurality of inlets 215, the administration may be performed via an administration channel 100, such as a duct, that is aligned along the intrabody device tip 299 or via a covering channel that covers a portion of the helical channel 200.

As described above, the administering and withdrawing of the liquid medical substance may be performed during a movement of the intrabody device, such as a catheter, along the target vein, for example during an introduction 251 and/or extraction 250 of the intrabody device, such as a catheter, into and/or from a target vein. Optionally, the intrabody device tip 299 is rotated during the movement. The rotating of the helically arranged outlets 215 during the movement allows releasing the liquid medical substance around a relatively large, optionally continuous, surface area of the venous wall 210. As the helical arrangement is stretched along the horizontal and vertical axes of the intrabody device tip 299, the rotation thereof substantially and/or fully covers an annular surface therearound.

Optionally, the arrangement of inlets is used as an arrangement of outlets. In such an embodiment, the withdrawing is similarly performed on a relatively large, optionally continuous, surface area of the venous wall 210.

Optionally, an additionally arrangement of outlets, optionally parallel, is added to the intrabody device tip 299, allowing the release of an additional liquid medical substance during, before and/or after the release of the liquid medical substance.

Optionally, the distance between the outlets 215 is less then 3 mm, 2 mm and/or 1 mm. In such a manner, the rotation allows fully cover the venous wall 210 during the rotation of the intrabody device tip 299.

It should be noted that the movement of the intrabody device tip 299 in combination with the rotation thereof allows covering venous wall 210 of substantially all along the latitudinal and longitudinal axes of a target vein.

Figure 5:
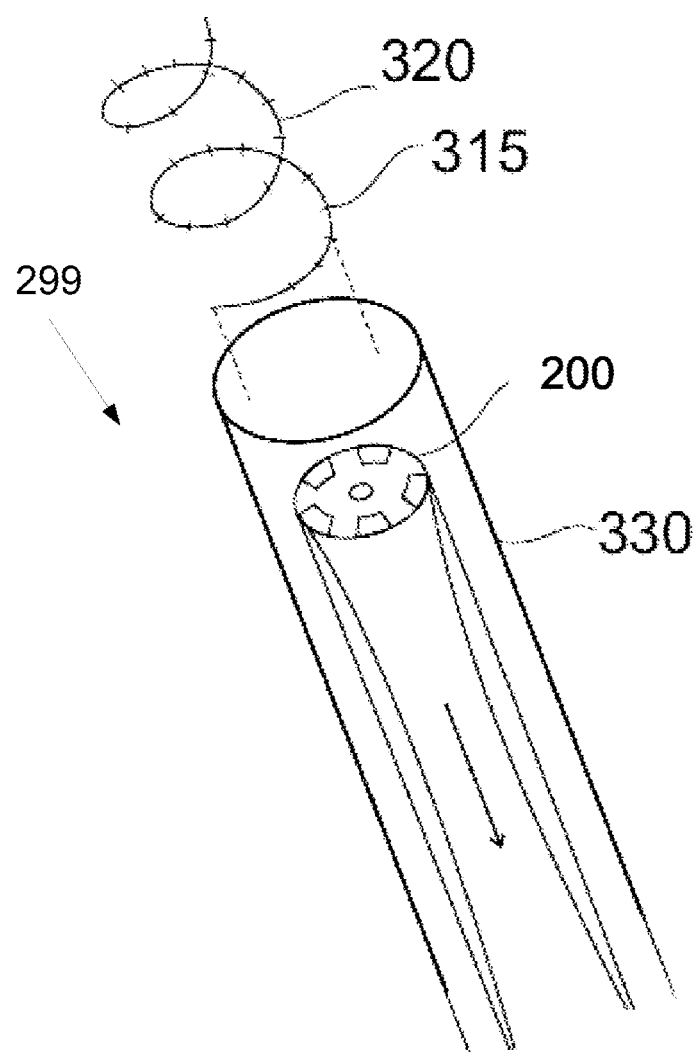
FIG. 5 is a schematic illustration of the intrabody device tip in FIG. 4 and an exemplary helical movement pattern thereof, according to some embodiments of the present invention.

Reference is now also made to FIG. 5, which is a schematic illustration of the intrabody device tip 299 in FIG. 4A and an exemplary helical movement pattern thereof 320, 315, according to some embodiments of the present invention. Optionally, the intrabody device tip 299 further comprises an external covering channel 330 with a helical track that is sized and shaped according to the pattern of the helical arrangement of inlets and/or outlets and spread along the inner wall thereof. For example, if the inlets and/or outlets are extended out from the axial profile of the helical channel 200, the helical track is turn or twist like a screw around them. In such a manner, the extraction and/or the insertion of the intrabody device tip 299 from and/or into the external covering channel 300 cause a helical movement of the arrangement, for example during the insertion of the helical channel 200 into the external covering channel 330 and allow a helical administration of the medical device and/or a helical withdrawing of the residue of the medical device.

According to some embodiments of the present invention, the intrabody device tip 299 having the helical arrangement of a plurality of outlets 215 which is described in FIG. 4A and an additional, optionally substantially parallel, helical arrangement of a plurality of inlets (not shown) for withdrawing a residue of a liquid medical substance, such as a sclerosing agent, according to some embodiments of the present invention. In such a manner, the rotating of the helically arranged inlets during the movement of the intrabody device tip 299 allows withdrawing the residue of the administered liquid medical substance around a relatively large surface area of the venous wall, similarly to the described above. As the helical arrangement is stretched along the horizontal and vertical axes of the intrabody device tip 299, the rotation thereof substantially and/or fully covers an annular surface therearound.

In use, the administering and withdrawing operations are optionally performed in a sequential manner. In such a manner, an administering of the liquid medical substance adjacently to a certain venous wall is accompanied with a withdrawing of the residue of the administered liquid medical substance adjacently to the certain venous wall. Optionally, an interaction period during which the liquid medical substance is passing to the walls is practiced between the administering and withdrawing operations. For example, the interaction period may be a 5 seconds period, a 10 seconds period, a 30 seconds period, and/or any intermediate or longer period.

Optionally, the withdrawing may be performed in a position that is shifted toward the blood circulation direction in the vein. In such a manner, the withdrawing operation may draw portions of the residue which have been shifted by the blood flow.

Optionally, the intrabody device tips, which are described above, are used for treatments near various branch veins, such as perforator veins. In such an embodiment, the withdrawing of the residue of a liquid medical substance, such as a sclerosing agent, may prevent the entering thereof to larger veins. The withdrawing of the sclerosing agents, together with the surrounding blood and/or debris substantially reduces or eliminates the likelihood of blood clotting, such as from the vein during the sclerosing procedure.

Figure 6:
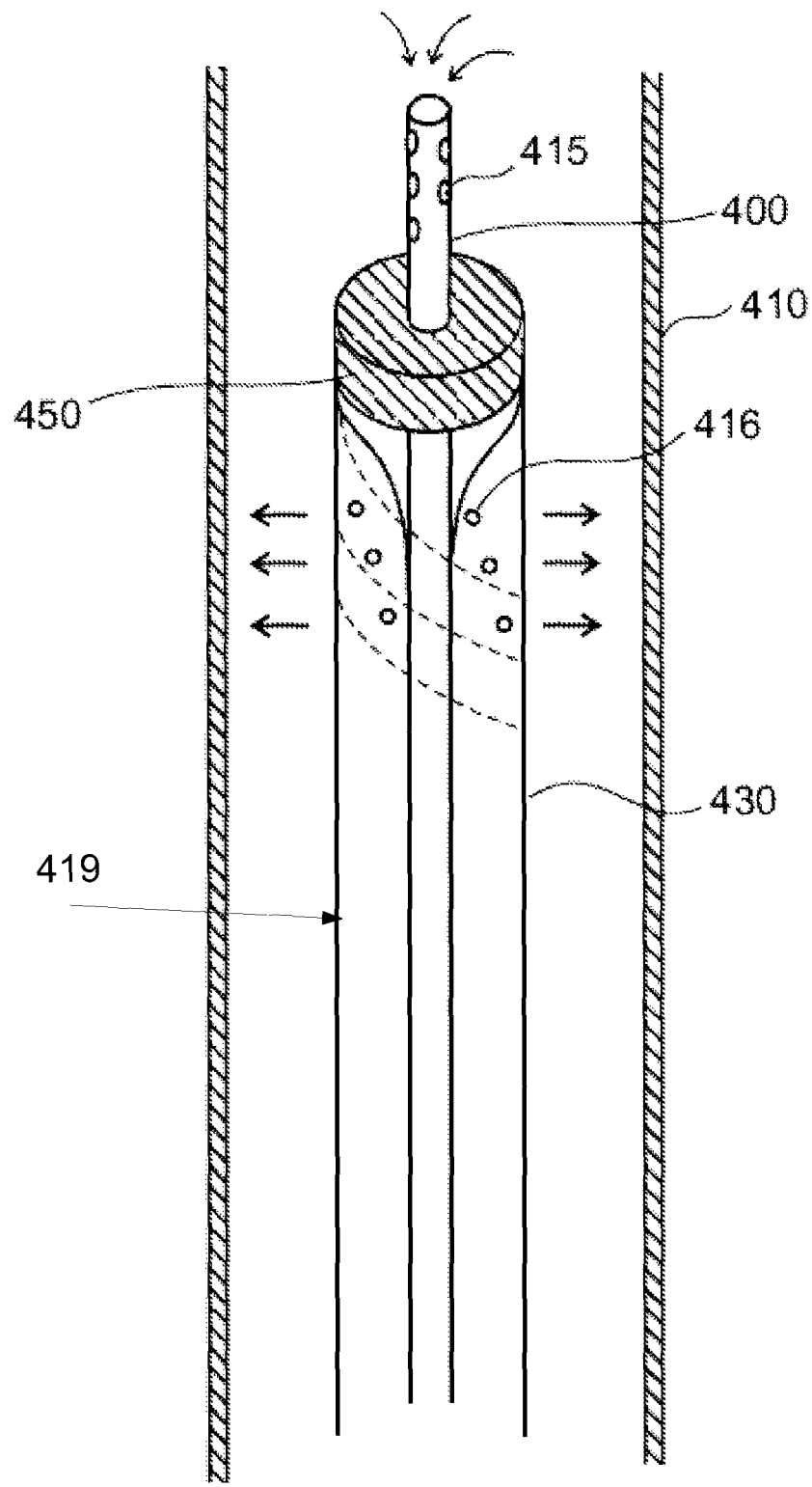
FIG. 6 is a schematic illustration of an intrabody device for administering a liquid medical substance, such as a sclerosing agent, along a portion of a venous wall and withdrawing the residue of the liquid medical substance from the distal end thereof, according to some embodiments of the present invention.

Reference is now made to FIG. 6, which is a schematic illustration of an intrabody device tip 430 for administering a liquid medical substance, such as a sclerosing agent, along a portion of a venous wall 410 that is parallel thereto and withdrawing the residue of the liquid medical substance from the distal end thereof, according to some embodiments of the present invention. In such an embodiment, the administered liquid medical substance is drawn from the distal end of the intrabody device tip 430 before arriving to venous spaces which outside of a target venous space that is optionally substantially in front of the intrabody device tip 430. Optionally, the intrabody device tip 430 comprises an administration channel 419, which is optionally a channel having an arrangement of outlets 416, optionally helical or annular, for administering the liquid medical substance along the longitudinal axis of the intrabody device tip 430. The arrangement of outlets 416, which are optionally nozzles or apertures, are perpendicular the longitudinal axis of the intrabody device tip 430 and therefore directs the liquid medical substance towards the venous walls. In addition, the intrabody device tip 430 comprises an extraction channel 400, which is optionally a channel having a smaller diameter than the diameter of the administration channel 419. For example, the diameter of the lumen of the extraction channel 400 may be 2 mm-4 mm and the diameter of the lumen of the administration channel 419 may respectively be 6 mm-8 mm. The extraction channel 400 is optionally positioned in the administration channel 419, allowing the conducting of the drawn residue of the liquid medical substance, optionally together with blood and debris, simultaneously, alternatively, and/or sequentially to the administration of liquid medical substance. Optionally, as shown at FIG. 6, the extraction channel 400 is a tubular, needle shape device. Optionally, a lumen block 450 is positioned at the distal end of the administration channel 419, preventing or substantially preventing from the liquid medical substance to flow therethrough. Optionally, extraction channel 400 comprises a plurality of inlets in its distal end 415 thereof. These inlets are optionally directed toward the venous walls, allowing the withdrawing of residue of the medial device from the proximity thereof. The directing of the inlets toward the venous walls creates a withdrawing force which is substantially perpendicular to the longitudinal axis of the intrabody device tip 430. Such a withdrawing force may function as a suction wall that does not allow or substantially does not allow the passage of liquid medical substance away from the distal end of the intrabody device tip 430. Such an embodiment may be used for treating veins in proximity to branch veins, such as perforator veins. Similarly to the described above, such an intrabody device tip allows administering liquid medical substances, such as sclerosing agents, in proximity to the venous walls.

Optionally, the withdrawing operation is performed during the administration of the liquid medical substance. In such a manner, the liquid medical substance is not or substantially not diluted by the blood. In this way the sclerosing agent, which may be administered directly on or near the vein walls, may be relatively effective even is relatively low concentrations of less than 5%, 3% or 1%. Furthermore, the withdrawing allows the physician to relatively easily control the quantity and the concentration of liquid medical substance that is administered in adjacent to a certain venous wall. As the blood is drawn from the administered area, the physician can determine the amount that is administered to a certain target tissue more efficiently.

As described above, the withdrawing is performed at the distal end of the intrabody device tip 430. In such a structure, withdrawing that is performed during a movement of the intrabody device tip 430 away from the distal end thereof, for example during the pulling out of the intrabody device tip 430, allows collecting residue of a liquid medical substance which have been released along the longitudinal axis of the intrabody device tip 430. Optionally, in use, the administration is performed along a certain segment of the venous wall, and then, optionally after an interaction period, the intrabody device tip 430 moves along the certain segment while the extraction channel 400 performs a withdrawing operation.

Figures 7A, 7B:
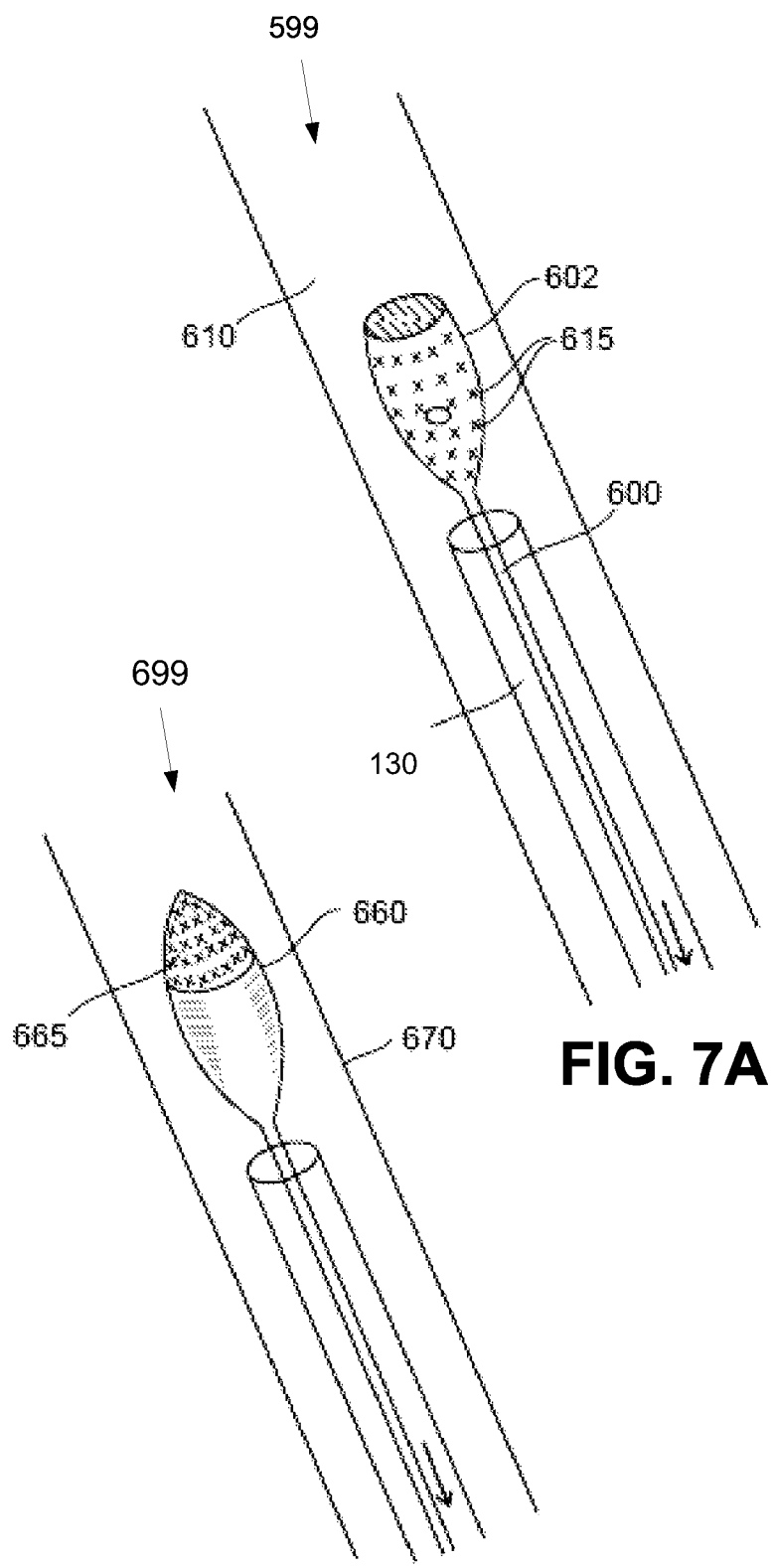
FIG. 7A is a schematic illustration of an intrabody device tip for administering a liquid medical substance via a filtering element, according to some embodiments of the present invention.
FIG. 7B is a schematic illustration of an intrabody device tip withdrawing a residue of a liquid medical substance, and optionally surrounding blood and debris, via a filtering element, according to some embodiments of the present invention.

Reference is now made FIG. 7A, which is a schematic illustration of an intrabody device tip 599 for administering a liquid medical substance via a filtering element 602, according to some embodiments of the present invention. The intrabody device tip 599 is optionally as described in FIG. 1. However, the intrabody device tip 599 comprises an administration channel with one or more outlets which are covered with the filtering element 602. Optionally, the filtering element 602 is an expandable element, for example a mesh of Nitinol strings and/or any flexible suitable material. Optionally, the filtering element 602 is expended substantially to the inner diameter of the vein. In such a manner, the administration may be performed in proximity to the respective venous walls. In addition, the filtering element 602 may determine a spatial releasing pattern, for example by defining a different pattern of releasing holes 615 and/or temporal releasing pattern, for example according to the diameter of the holes thereof. Optionally, the filtering element 602 may comprise a liquid medical substance, such as a sclerosing agent.

Reference is now made to FIG. 7B, which is a schematic illustration of an intrabody device tip 699 for withdrawing a residue of a liquid medical substance, and optionally blood and debris, via a filtering element 665, such as a mesh, a net, and/or a grating, according to some embodiments of the present invention. The intrabody device tip 699 is optionally as described in FIG. 7. However, the intrabody device tip 699 comprises an extraction channel that performs the aforementioned withdrawing via the filtering element 665. The filtering element allows preventing from the filtered debris to block the extraction channel or the duct that is connected thereto and for conducting the residue of the liquid medical substance, blood, and debris away from the target vein. The filtering element 665 collects debris which has a diameter above a certain threshold. Optionally, as described above, the filtering element 665 may be expended to touch the venous walls. In some embodiments, the filtering element 665 may be used to prevent materials in the vein from entering into the area 670 where the liquid medical substance is administered. In other embodiments, the filtering element 665 may be used to collect debris in a designated cavity 660 and/or other non-required elements from within the vein when intrabody device tip 699 is polled out from the target vein. For example, the filtering element 665 may be expanded to be adjacently positioned to vein walls, and when pulled backwards against the direction of blood flow, it may collect drugs, sclerosing agent, and/or other content from within the vein, therefore allowing the target vein or respective venous walls to be substantially cleaned out of unwanted materials.

It is expected that during the life of a patent maturing from this application many relevant methods and devices will be developed and the scope of the term a sclerosing agent, a liquid medical substance, a filtering element, and an intrabody device, such as a catheter, is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for administering a liquid medical substance in a vein, comprising:
    inserting an intrabody device having an intrabody device tip and at least one administration duct and at least one withdrawing duct into a target venous lumen;
    performing the following while moving the intrabody device tip along said target venous lumen:
        applying, at a first direction, a medical liquid quantity of a liquid medical substance in an ejection pressure for ablating said venous lumen via at least one outlet of said at least one administration duct in said intrabody device tip for the administering of said liquid medical substance toward a venous wall at said target venous lumen; and
        applying a suction pressure to withdraw at a second direction a residue quantity of a residue of said liquid medical substance from said target venous lumen: via said at least one withdrawing duct, said suction pressure is applied via first and second inlets of said at least one withdrawing duct in said intrabody device tip;
    wherein a relation between said ejection pressure, said medical liquid quantity and said first direction and said suction pressure, said residue quantity and said second direction limits the medical liquid quantity within said venous lumen to a limited space of less than 4 cubic centimeter centered around any of the at least one outlet while the intrabody device tip is moved along said target venous lumen;
    wherein said at least one outlet is placed along said at least one administration, between said first inlet and said second inlet;
    wherein said withdrawing and said administering are performed simultaneously.

2. The method of claim 1, wherein said liquid medical substance comprises a sclerosing agent.

3. The method of claim 2, wherein said sclerosing agent concentration is lower than 5 percent.

4. The method of claim 1, wherein said withdrawing is performed a predefined period after said administering being completed.

5. The method of claim 1, wherein at least one of said ejection pressure, quantity and direction and said suction pressure, quantity and direction is performed according to a characteristic of said target venous lumen.

6. The method of claim 1, wherein said ejection direction is substantially perpendicular to movement axis of said venous wall.

7. The method of claim 1, wherein said administering is performed in a plurality of ejection directions.

8. The method of claim 1, wherein said at least one administration duct and at least one withdrawing duct are connected to the tip of said intrabody device, at least one of said administering and withdrawing is performed via said intrabody device tip while said intrabody device tip being in motion.

9. The method of claim 1, wherein at least one of said administering and withdrawing is performed in a helical pattern having a central axis substantially parallel to said venous wall.

10. The method of claim 1, wherein said administering comprises substantially blocking a blood flow in said target venous lumen.

11. The method of claim 1, wherein said withdrawing is applied from a plurality of suction directions.

12. The method of claim 11, wherein a first of said plurality of suction directions is directed toward a first edge of said venous lumen and a second of said plurality of suction directions is directed toward a second edge of said venous lumen.

13. An intrabody device for administering a liquid medical substance in a vein, comprising:
    a catheter having an insertion tube having plurality of tubular ducts:
    an intrabody tip having at least one outlet and at least one inlet of said plurality of tubular ducts;
    an ejection force source connected to at least one first tubular duct of said plurality of tubular ducts and applies an ejection force for conducting therethrough a liquid medical substance to said at least one outlet for administering said liquid medical substance at an ejection pressure, quantity and direction; and a suction force source connected to at least one second tubular duct of said plurality of tubular ducts and applies a suction force for withdrawing therethrough a residue of said liquid medical substance from said at least one inlet in a suction pressure, quantity and direction;

a controller mechanism which controls said ejection force source and said suction force source to apply simultaneously said ejection force and said suction force while said intrabody device tip is moving along said venous lumen, wherein when said at least one inlet and outlet are in a venous lumen and a relation between said ejection and suction pressure, quantity and direction limits the extent of said liquid medical substance within said venous lumen to a predefined space.

14. The intrabody device of claim 13, further comprising an ejection channel with said at least one outlet and a withdrawal channel with said at least one inlet at the tip of the intrabody device, said withdrawal channel is partly encircled by said ejection channel.

15. The intrabody device of claim 13, wherein said at least one inlet comprising a plurality of inlets, said at least one outlet is positioned between at least two of said plurality of inlets.

16. The intrabody device of claim 13, further comprising a helical ejection channel having said at least one outlet positioned therealong.

17. The intrabody device of claim 13, further comprising a helical withdrawal channel having said at least one inlet positioned therealong.

18. The intrabody device of claim 13, further comprising a filtering element positioned in front of said at least one inlet and configured for preventing from at least one component having a diameter above a certain threshold from penetrating said at least one inlet.

19. The intrabody device of claim 18, wherein said filtering having a cavity for collecting said at least one component.

20. The intrabody device of claim 13, further comprising a filtering element positioned in front of said at least one inlet and configured for determining at least one of said suction pressure, quantity and direction.

21. The intrabody device of claim 13, further comprising a filtering element positioned in front of said at least one outlet and configured for determining at least one of said ejection pressure, quantity and direction.

22. The intrabody device of claim 13, further comprising an intrabody device tip having a portion having said at least one outlet and an expended and unexpended configurations, wherein a distance between said at least one outlet and a venous wall in said venous lumen is reduced when said portion being in said expended configuration.

23. The intrabody device of claim 13, wherein said at least one outlet are arranged to allow said administering in a helical pattern.

24. The intrabody device of claim 13, wherein said at least one inlet has a plurality of suction directions.

25. The intrabody device of claim 13, wherein said relation sets the concentration of said liquid medical substance in said predefined space.

26. The intrabody device of claim 13, wherein said controller mechanism is a dual syringe.

27. The intrabody device of claim 13, wherein said inserting induces the collapse of said target venous lumen.

* * * * *